United States Patent [19]

Scriven, II et al.

[11] 4,250,741

[45] Feb. 17, 1981

[54] PRECISION SPINNING DROP INTERFACIAL TENSIOMETER

[75] Inventors: L. Edward Scriven, II, Minneapolis, Minn.; Yee Seeto, Jurong Town, Singapore; Carl D. Manning, Charleston, W. Va.

[73] Assignee: The Regents of the University of Minnesota, Minneapolis, Minn.

[21] Appl. No.: 34,644

[22] Filed: Apr. 30, 1979

[51] Int. Cl.³ .......................................... G01N 13/02
[52] U.S. Cl. ..................................................... 73/64.4
[58] Field of Search ......................................... 73/64.4

[56] References Cited

PUBLICATIONS

Torza, S. *The Rotating-bubble Apparatus*, in Rev. Sci. Instr. 46(6): p. 778–783. Jun. 1975.

*Primary Examiner*—Gerald Goldberg
*Assistant Examiner*—Joseph W. Roskos

*Attorney, Agent, or Firm*—Burd, Bartz & Gutenkauf

[57] ABSTRACT

An improved instrument for the precise measurement of interfacial tension between two fluid phases by means of a drop of the less dense fluid surrounded by the more dense fluid, both fluids spinning together in gyrostatic equilibrium. Elements of the invention eliminate departures from gyrostatic equilibrium which went unrecognized in the prior art. These elements are based on hydrodynamic principles unknown in the prior art. The instrument is characterized by the combined use of air bearings and sample-holder mountings which reduce vibrations and eccentricities, eliminate temperature gradients within the sample, and assure that interfering hydrodynamic flows are suppressed. Other improvements include biprecision sample tube, full visual access to the spinning drop, leveling provisions, timing belt transmission, avoidance of bearing heating and wear problems, and convenient control of sample temperature.

12 Claims, 4 Drawing Figures

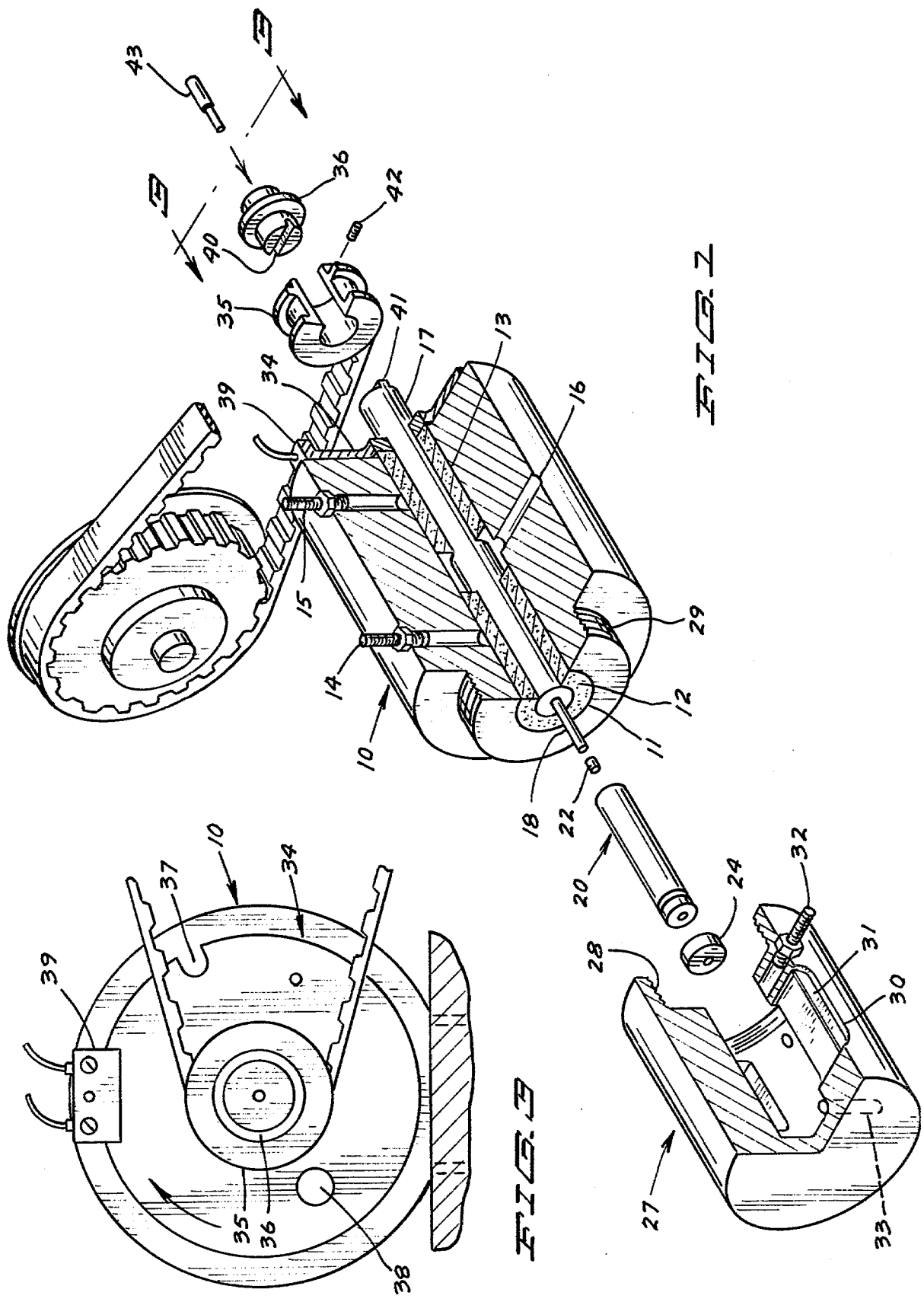

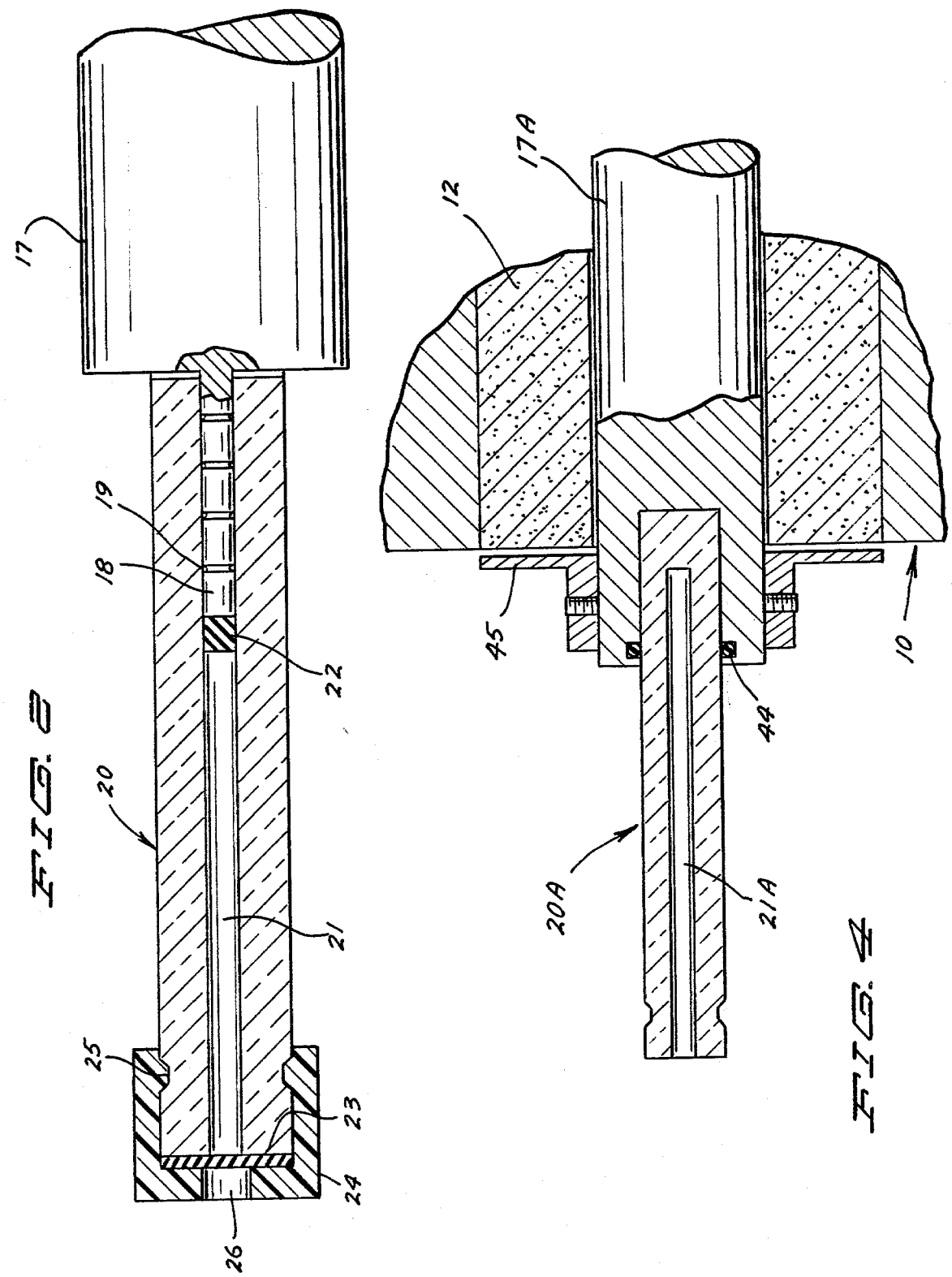

PRECISION SPINNING DROP INTERFACIAL TENSIOMETER

BACKGROUND OF THE INVENTION

1. Field of the Invention

The invention pertains to the measurement of surface or interfacial tension between two fluid phases, gas and liquid or liquid and liquid. This basic physical property of fluid interfaces is important to most fields of technological art in which gas-liquid and liquid-liquid interfaces or menisci occur, including but not limited to detergency, solubilization, microemulsification, emulsification, demulsification, foaming, defoaming, aeration, absorption, distillation, extraction, metallurgical and polymeric melt processing, crystal growing, various fluid phase reaction methods, and formulations of wetting agents, spreading agents, lubricants, drilling fluids for well-drilling, adhesives, paints, coatings, photographic films, chemical solutions for enhanced oil recovery, etc.

The invention pertains to the measurement of all magnitudes of interfacial tension but is especially advantageous for measurement of tensions less than 1 dyn/cm ($10^{-3}$ newton/meter) and is even more advantageous for measurement of tensions less than $10^{-2}$ dyn/cm ($10^{-5}$ newton/meter). It is also advantageous for measurements at temperatures substantially different from ambient.

2. Description of the Prior Art

Conventional methods of measuring fluid interfacial tensions are the force methods, the shape methods, and several miscellaneous methods. The principal force methods are the well-known techniques of the Du Noüy ring and the Wilhelmy plate. These methods are generally not suitable for tensions less than 1 dyn/cm, because the force becomes too small to be accurately measured. The principal shape methods are the sessile drop and the pendent drop, both well-suited for low interfacial tension measurements. Other miscellaneous methods include the differential capillary rise, drop weight, maximum bubble pressure, and light scattering techniques. Though capable of measuring low tensions, they are not widely used owing not only to the tedious measurement procedure involved, but also to other requirements and limitations. The state of art is summarized by A. W. Adamson, *Physical Chemistry of Surfaces*, 3rd edition, Wiley (1976).

The spinning drop technique is a shape method but is not conventional. The method, first devised by Vonnegut in 1942 (B. Vonnegut, Rev. Sci. Instr. 11 6 (1942)), has received its development in connection with low interfacial tensions:

Silberberg (A. Silberberg, Ph.D. Thesis, University of Basel, Switzerland, 1952) measured low tensions in a polymer system by means of the spinning drop method. He noted the effects of bearing heating and the consequences on the tension.

Princen et al (H. M. Princen, I.Y.Z. Zia and S. G. Mason, J. Colloid Interface Sci. 23, 99 (1967)) solved the spinning drop shape problem by means of elliptic integrals and showed how to solve explicitly for the tension. They developed a variable speed spinning drop apparatus for measuring surface and interfacial tensions. But instead of measuring drop diameter they chose to measure drop length and volume and from these to calculate tension. The reason evidently is that this approach avoids the need to determine the cylindrical lens effect of the sample tube. It depends on the drop volume remaining constant at the volume injected, which is often violated.

Ryden and Albertsson (J. Ryden and P. Albertsson, J. Colloid Interface Sci. 37, 219 (1971)), using essentially the method of Princen et al, measured ultralow tensions (<0.01 dyn/cm) in a phase-separated polymer system. Their operating speed range of 200 to 450 rpm may sometimes be suitable for viscous polymer systems but is too low to achieve needed gyrostatic equilibrium in less viscous systems.

Patterson et al (H. T. Patterson, K. H. Hu and T. H. Grindstaff, J. Polymer Sci. Part C, 34, 31 (1971)) modified the method for measuring tensions of molten polymer solutions. They measured the drop diameter photographically and used experimentally-determined magnification factors in their calculation of tensions from measurements.

Torza (S. Torza, Rev. Sci. Instru. 46, 778 (1975)) designed a spinning drop apparatus using air bearings to avoid bearing heating and a magnetic coupling to reduce vibration. The instrument is relatively vibration free up to 7,000 rpm, but not beyond. It employed a comparatively large diameter of sample tube.

Of the spinning drop instruments described, all but Silberberg's and Ryden and Albertsson's were designed for measuring relatively high tensions. Cayias et al (J. L. Cayias, R. S. Schechter and W. H. Wade, in *Adsorption at Interfaces* (edited by K. L. Mittal), ACS Symposium Series 8, pp. 234-247 (1975)) much improved the method in an attempt to accommodate ultralow interfacial tensions. Their design, known as the University of Texas Spinning Drop Interfacial Tensiometer, has become widely used for low tension measurements in the petroleum recovery art. The design is also copied and attempts have been made to improve upon it.

Gash and Parrish (B. Gash and D. R. Parrish, J. Pet. Tech. 29, 30 (1977)) developed a constant-speed spinning drop apparatus for surfactant screening. They mounted the sample tube directly to the motor shaft by an aluminum collar, which avoided the use of bearings. The relatively low operating speed of 3,600 rpm is probably not sufficiently high to ensure gyrostatic equilibrium, and vibration may be serious.

The evolution of the spinning drop method shows that no previous investigators correctly recognized the nature of departures from gyrostatic equilibrium which are brought about by vibrations, eccentricity, varying speed, bearing heating and temperature variations. Only Torza tried air bearings but he did not consider the matter of coaxiality. In his measurements he avoided drop diameter and relied on constancy of drop volume, which is not uncommonly inconstant, especially in low tensions systems.

No previously described instrument has adequate provisions for establishing that gyrostatic equilibrium is approached closely enough by the contents of the sample tube to permit reliable measurements of interfacial tension.

No previously described instrument has been designed on the basis of hydrodynamic principles and an analysis of all of the expected errors. Shortcomings of previously described instruments include bearing heating and non-isothermal sample holder, lack of coaxiality of the bore of the sample holder and the rotation axis, vibrations from bearings and motor, limited visual access to the sample holder, absence of provision for sample holders of different inside diameters, insufficiently high rotational speeds, and inadequate provision for leveling the axis of rotation.

SUMMARY OF THE INVENTION

The improved precision spinning drop interfacial tensiometer according to the present invention includes a massive bearing housing supported on a massive base having three-point leveling means. A pair of porous bushings are tandemly aligned within the bearing housing. Compressed air inlet and outlet ports are provided in the bearing housing. A precision ground shaft is journaled in the bushings. A biprecision transparent isothermal sample tube is secured at one end to one end of the shaft for precise coaxial rotation with the shaft. The opposite end of the sample tube is closed by sealing means. A sample holder housing encloses the sample tube. The sample holder housing is removably secured to the bearing housing. Aligned windows are provided in the sample holder housing to permit viewing of the sample tube. Gas inlet and outlet ports are provided in the sample holder housing to permit sample temperature control. Power means are provided for rotating the shaft and sample tube in the air bearings at a constant rotational speed sufficient to maintain gyrostatic equilibrium. Means are provided for measuring the rotation of the shaft and further means are provided for positioning the shaft axially in the bearing housing.

BRIEF DESCRIPTION OF THE DRAWINGS

The invention is illustrated in the accompanying drawings in which:

FIG. 1 is an exploded perspective view, partly in section, showing details of construction of the instrument;

FIG. 2 is an elevation, in section, showing details of a coaxial spindle mount for a sample tube;

FIG. 3 is an end elevation of the bearing housing on the line 3—3 of FIG. 1 and in the direction of the arrows; and FIG. 4 is an elevation, in section, showing an alternative sample tube mount and shaft axial positioning disc.

DETAILED DESCRIPTION OF THE PREFERRED EMBODIMENT

Referring now to the drawings, and particularly to FIG. 1, there is shown a massive aluminum air bearing housing 10 having a central longitudinal bore 11. A pair of porous bushings 12 and 13 (Airlub Model LB-5, 0.5 in. i.d. and 1.9 in. long, Dico Bearings Specialty Co., Boston, Mass.) are carefully aligned in tandem in the bore 11 of housing 10. Bearing housing 10 is provided with inlet ports 14 and 15 for introduction of compressed air to the bushings and outlet port 16 is provided for discharge of some of that air; the remainder of the air escapes at the outer ends of the bushings. Coaxiality of the bearings is critical.

The bearings support a shaft 17 made from precision ground 303 stainless steel, 0.5 in. nominal diameter and 5.5 in. long (Dico Bearings Specialty Co., Boston, Mass.). The shaft is custom ground and polished for 0.0015 to 0.0020 in. diametrical clearance with the air bearings. One end of shaft 17 is turned down and custom ground to form a 7/16 in. long coaxial spindle 18 for close fitting (about 0.0001 in. diametrical clearance) into the bore of a sample holder 20. Spindle 18 is desirably provided with peripheral grooves 19.

Sample holder 20 is a biprecision Pyrex glass tube of inner and outer concentricity ±0.0005 cm. As one example, sample holder 20 is about 0.19 cm i.d. and 0.65 cm o.d. (Precision Electronics Glass, Inc., Vineland, N.J.) cut 5 cm long and glued to the grooved spindle and shaft shoulder with epoxy cement, as best seen in FIG. 2. A Teflon plug 22 4 mm long is square cut and pressure fitted (0.0005 in. diametrical interference) into the tube bore to prevent the liquid sample within the sample holder from contacting the spindle.

The open end of tube 20 is sealed by a silicone rubber disc 23 pressed into place by a Teflon cap 24 which has an interior rim flange that snaps into a groove 25 ground into the tube exterior. Cap 24 also has a central hole 26 to permit penetration of the seal-sealing disc 23 by a hypodermic needle when, in the final step of the sample loading procedure, the filled tube is pushed vertically downward into the cap and excess liquid must be expelled.

A Lucite housing 27 is removably secured to air bearing housing 10 as by the internally threaded open end 28 of housing 27 engaging externally threaded bearing housing portion 29. Sample holder housing 27 is provided with a pair of windows 30 fitted with optically flat glass panes 31. Housing 27 forms an enclosure for sample tube 20 and its thermostated air bath. Inlet 32 and outlets 33 are provided for the flow of cooling air or other temperature control gas through the sample holder housing.

The driven end of shaft 17 carries a slotted aluminum disc 34 for revolution counting, a double-flanged timing belt pulley 35 (No. 16XL037, Plastock, Inc., West Nyack, N.Y.) and a grooved aluminum cap 36. Disc 34 has a slot 37 and a diametrically opposed hole 38 so drilled as to compensate dynamically for the slot. A rotation sensor 39 (Model H13B2, Photon-Coupled Interruptor Module, General Electric Co., Fairfield, Conn.) is mounted on bearing housing 10 astride the rim of slotted disc 34. Cap 36 is provided with a groove 40 which engages the end tongue 41 of shaft 17, and a set screw 42 which holds the cap seated on the end tongue of the shaft. Disc 34, pulley 35 and cap 36 are cemented together into one piece which is dynamically balanced by the addition and removal of small amounts of material, as necessary, a crucial adjustment. The disc-pulley-cap piece can be fastened and unfastened from different shaft and sample holder assemblies.

Shaft 17 is positioned axially by the pressure against slotted disc 34 exerted by air escaping from the adjacent air bearing 13, and by the pressure of an air jet 43 directed axially at the set screw. So long as the timing belt is properly located, these pressures suffice.

A 1/10 hp D.C. motor-generator (Electro-Craft E-586-MG, Electro-Craft Corp., Hopkins, Minn.) single flanged drive pulley (No. 48XL037, Plastock, Inc.) and timing belt (No. 130XL037, T. B. Wood's Sons Co., Chambersburg, Pa.) give a 3:1 speed-up ratio without slipping. This arrangement also helps the air bearings to isolate the sample holder from any vibrations in the motor shaft. Belt location and tension are controlled by adjustments in the motor mount. Too little tension results in axial wobble, particularly at lower speeds. Too much causes the shaft to graze the bearings dangerously, particularly at higher speeds. In full adjustment, radial runout at the spindle end turning up to 4,000 rpm is ±0.0001 in. as measured by a dial indicator. Observation and photography through the microscope indicate less runout than this above 12,000 rpm, evidently because of the hydrodynamic self-centering action of the shaft spinning in the air bearings. Calculations indicate that the maximum operating speed of 15,000 rpm is well below the critical speeds for lateral bending vibrations of both the shaft and the sample holder.

The drive unit has a 5,000 rpm maximum speed, delivering torque up to 20 oz.-in. for continuous and stable operation. Current measurements indicate that the complete instrument requires less than 8 oz.-in at maximum speed, i.e., when the shaft and holder assembly turns at 15,000 rpm. A speed control unit (Electro-Craft E-586-0) provides better than 0.3 percent speed stability over the entire speed range of the motor, as determined by measurements on the complete instrument.

Compressed air for the air bearings is drawn from a supply source through a pressure regulator and two air filters (Model B5A, Commercial Filters Corp., Lebanon, Ind.) in series. Pressure of from 45 to 50 psig is required for instrument speeds in the range of 10,000 to 15,000 rpm. The air bearings and motor are protected from damage by an adjustable, pressure activated mercury switch (Model L604A, Honeywell Corp., Minneapolis, Minn.) coupled to a relay which breaks the motor circuit whenever the air supply pressure drops below the required level.

In FIG. 4 there is shown an alternative sample holder and receptacle mount. The alternative sample tube 20A is closed at one end (with a nearly flat bottom inside) and this end slides into a precisely bored receptacle in the end of shaft 17A. Though the slide-fit is adequate when liquid wetted, a rubber O-ring shoulder 44 provides a slight pressure-fit and thus a vacuum seal to guarantee that the sample holder remains fixed in the spinning assembly. When this alternative receptacle mount is employed, in order to maintain the axial position of the shaft, air jet 43 is replaced by an unslotted aluminum disc 45 positioned at the sample holder end of shaft 17. With about 1/32 in. clearance between them and the ends of the air bearings, the air escaping past the discs at both ends of the shaft provides opposed thrust-bearing action which gives excellent axial positioning. With this alternative sample holder and receptacle mount, radial runout measurements at the receptacle bore indicate radial runout of about ±0.00015 in. and less.

The tensiometer instrument is mounted on a massive cast iron base with three legs resting on rubber pads to help damp any vibrations. Two of the three legs are adjustable screws for leveling the axis of rotation of the sample holder, a vital provision. In an earlier design, the local heating by ball bearings causes axial temperature gradients which often induce flows that hold a drop close to a particular axial location. Vibration-induced flows might have the same effect in some instances. In the present instrument, these perversions of gyrostatic equilibrium are suppressed leaving the drop in neutral equilibrium with respect to axial translation if the rotation axis could be made perfectly horizontal. Of course, it cannot be. Moreover, a compromise has to be struck between the damping action of the mounting pads and the accuracy and endurance of a leveling on them. With very careful leveling, a drop typically takes four to six hours to migrate axially to the ever-so-slightly higher end of the sample holder. The rate depends on not only misalignment, but also the density difference, viscosity (primarily of the denser fluid), angular velocity and dimensions of the drop and the tube containing it. For long runs, it is advisable to check and adjust leveling every few hours, an inconvenience which is the price of eliminating convection.

MEASUREMENT PARTICULARS

To determine interfacial tension with a spinning drop instrument requires measuring the rotational speed and diameter of a drop of appropriate size. In addition, gyrostatic equilibrium must be established and, external to the tensiometer, fluid densities must be measured.

Rotational speed is measured with a digital frequency counter (Model 5381A, Hewlett-Packard Co., Santa Clara, Calif. or, for testing and comparison, a Model 6A75, Atec, Inc., Houston Tex.) activated by the rotation sensor 39 astride the slotted disc 34. The pulse signals from the latter can also be used to synchronize a strobe light. The three counter gate times of 0.1, 1, and 10 sec. are convenient for testing, but the longest is used for accurate measurement and gives a resolution of 0.1 cycle/sec. in the quotient of the number of cycles counted and the counting period, 10 sec. Speed stability of the instrument was determined with each of the counters and a temporarily mounted, double-slotted aluminum disc; the resolution of the counter display was limiting but could have been overcome by using a disc with four or more slots. The results indicated 0.34 percent or better speed stability at 4,700 rpm and 0.17 percent at 11,000 rpm. A multiway switch wired to the interruptor module of each apparatus allows speed measurements to be made on four or more instruments successively with only one frequency counter. A similar switch enables a single stroboscope to be used for several instruments when synchronized illumination is desired during diameter measurement in each.

Apparent drop diameter is measured with accuracy 0.0001 cm by means of a bifilar micrometer microscope (Model 110A, Gaertner Scientific Corp., Chicago, Ill.) and, when wanted, drop length is found with the aid of a micrometer slide (Gaertner) built into the microscope assembly. This assembly is fastened with set screws into slots machined in an arm of the instrument base. Alternatively, it is fastened to a separate, movable base which can be brought successively into registry with different instrument bases when more than one apparatus is being used. Being fastened to a separate base, the microscope can be adjusted without preturbing the leveling of the instrument proper. This is particularly advantageous for runs in which a drop is kept spinning for hours or days.

The instantaneous image of the drop is shifted and distorted by non-uniformities in the glass wall of the sample holder. Most significant are departures of the inner and outer surfaces from concentricity; azimuthal variations in the radii are generally smaller (owing to the surface tension of glass above the fictive temperature). Analysis by ray optics shows that typical eccentricity (0.002 to 0.003 cm) in selected precision-bore glass tubing can cause up to 0.5 percent error in apparent drop diameter. Moreover, for drop diameters less than 0.01 cm the image shifts vertically up to 30 percent away from the rotation axis, once per revolution. The eye is unable to resolve the instantaneous image of the drop and a synchronized strobe light is required to avoid positional blurring. Biprecision tubing is needed for these reasons as well as for external centering when the alternative receptacle mounting is employed. The sample holders used cause an insignificant error of 0.08 percent in instantaneous apparent drop diameter when the eccentricity is 0.0005 cm. This fact, together with the coaxiality of sample holder and shaft, and the smooth running of the latter, permit accurate measurement of apparent drop diameter in continuous lighting, provided the drop is not too small and gyrostatic equilibrium is attained. However, when drop diameter is less than 0.02 cm, the 0.0005 cm eccentricity causes enough blurring to generate 2 percent uncertainty in diameter, and synchronized stroboscopic lighting becomes desirable. Otherwise such illumination is optional except for purposes of checking, whereas it is necessary to achieve the maximum precision possible with earlier instrument designs.

The cylindrical lens effect of the sample holder must be compensated by a magnification factor M to arrive at the true drop diameter. A fractional error in M produces triple the fractional error in interfacial tension deduced from the measurements (see equation below). The factor M can be found by measuring the apparent diameters of the low-density, cylindrical bodies of known diameters that float in sample liquid and therefore center themselves on the axis of the spinning tube. However, tests showed that M varies severely with different liquid fillings and quite significantly with temperature. Evaluating M experimentally can become time consuming.

In a theoretical treatment by ray optics which has been overlooked by many later workers, A. Silberberg (Ph.D. Thesis, University of Basel, Switzerland, 1952) showed that in the ideal case of a perfectly cylindrical tube, M is equal to $\eta'$, the refractive index referred to air of the denser fluid which surrounds the drop. This index is within 0.03 percent of $\eta$, the refractive index referred to vacuum. Hence $D=D_{app}/\eta$ where D and $D_{app}$ are the true and apparent diameters, respectively, of the drop of less dense fluid. To compare this relation with M, refractive indices $\eta$ of from 1.3442 to 1.6564 were determined for seven liquids with a refractometer (Bausch and Lomb). Direct measurements of M with three different floats and these liquids in each of three selected precision-bore sample holders about 0.19 cm i.d. and 0.65 cm o.d. agreed with the values of $\eta$ with standard deviation of 1.1 percent and maximum deviation of 1.4 percent. These deviations are attributable to the uncertainties in measuring the float diameters and to the eccentricities of the sample holders, which were not of biprecision tubing. Indeed, stroboscopic lighting was required and when it was desynchronized slightly the apparent diameter of a float varied periodically in time.

The conclusion is that the magnification factor M can be replaced by the refractive index $\eta$, which is easily determined outside the sample tube, and the error is certainly less than 1.4 percent. With biprecision tubing the error is very probably the uncertainty in $\eta$, namely less than 0.02 percent with the refractometer used in conjunction with the new instrument. Densities are readily found with an accuracy of 0.0001 g/cm³ with an oscillating tube precision digital density meter (PAAR Model DMA 40, Mettler Instrument Corp., Princeton, N.J.).

An indirect test for gyrostatic equilibrium is to measure tension at different rotational speeds; a direct test is by synchronized flashing illumination to "stop" the spinning sample holder or motion within it so as to reveal any relative movement. The sample holder is "stopped" by once every shaft revolution triggering a stroboscope (Strobotac Model GR 1531, General Radio Co., West Concord, Mass.) with the signal from the photo interruptor. This stroboscope has an internal oscillator for flashing-rate control when not externally triggered and is well suited to testing for gyrostatic equilibrium and to visualizing the flows inside the sample holder when gyrostatic equilibrium is absent.

ANALYSIS OF INHERENT MEASUREMENT ERRORS

The basic formula for interfacial tension from spinning drop measurements when written in terms of apparent drop diameter $D_{app}$ and denser fluid refractive index $\eta$ becomes the working formula:

$$\sigma = \Omega^2 D_{app}^3 \Delta\rho / 32\eta^3$$

The error in $D_{app}$ depends on the resolution (0.0001 cm) of the microscope and the eccentricity (0.0005 cm) of the biprecision-tubing sample holder. The former dominates drop sizes up to about 0.2 cm, and the latter becomes significant beyond. Thus the error ranges from 1.4 percent for a 0.01 cm diameter drop to 0.1 percent for a 0.2 cm drop and still less for larger ones. The error in $\Omega$ is less than 0.3 percent, that in $\eta$ is less than 0.02 percent, and that in $\Delta\rho$ is less than 0.3 percent provided the density difference exceeds 0.05 g/cm³. The approximation error in the basic formula itself is less than 0.1 percent provided the length L of the spinning drop is not less than five times its equatorial diameter, i.e., $L/D \geq 5$, and is less than 0.4 percent when $L/D \geq 4$.

Summarizing the error analysis, generally the contribution from diameter measurement is controlling when diameter is small, whereas the contribution from speed measurement becomes controlling at the larger drop diameters associated with tensions down to, say, 6 dyn/cm when $\Omega = 5,000$ rpm and $\Delta\rho = 0.2$ gm/cm³. (A variable is labeled "controlling" if it contributes 80 percent or more of the estimated error.) A range of uncertainty in speed control and speed measurement exists in the new instrument; correspondingly the expected error is about 1 percent when $D_{app} = 0.05$ cm and is less at larger $D_{app}$. Unless the densities of the two phases are close, the tensions corresponding to this diameter span are 0.08 dyn/cm and higher. Our rule is to use the lowest speeds $\Omega$ that satisfy the requirement of gyrostatic equilibrium. For a given tension, $D_{app} \propto 1/\Omega^{2/3}$ and so lower speed brings larger drop diameter and more accurate diameter measurement. The speed should remain fast enough that $L/D > 4$ or 5, however; otherwise the equation must be augmented by a shape factor.

In the ultralow tension range, $\sigma < 0.01$ dyn/cm, speeds in the range 5,000–6,000 rpm are often satisfactory. Then $D_{app}$ typically is less than 0.02 cm, the precision-limiting factor is optical resolution, the fractional error in $\sigma$ is inversely proportional to $D_{app}$, and the level of error expected in determining ultralow tensions is 2 percent or more, being larger the lower the tension. Because the limitation is optical resolution, this error probably cannot be reduced significantly by further refinements in design.

EXAMPLES

Results with three systems that bridge several orders of magnitude of tension are compared with literature values in the Table:

| Example | System | Precision Spinning Drop Interfacial Tensiometer[a] | UT Spinning Drop Interfacial Tensiometer[a] | Literature Values |
|---------|--------|---------------------------------------------------|---------------------------------------------|-------------------|
| | COMPARISON OF INTERFACIAL TENSION MEASUREMENTS AT 23 ± 1° C. | | | |
| I | n-decane/water (equilibrated) | 45.70 ± 0.30 | 45.85 ± 0.33 | 46.2 dyn/cm[b] |
| II | n-butanol/water (equilibrated) | 1.620 ± 0.004 | 1.637 ± 0.004 | 1.88 dyn/cm at 27° C.[c] 1.77[d] 1.83[e] 1.47[f] |
| III | n-octane/ surf. soln.[g] | 0.0023 ± 0.0002 | 0.0018 ± 0.0002 | 0.001 dyn/cm at 27° C.[c] |

[a]Listed range is one standard deviation above and below the mean.
[b]A. S. Michaels and E. A. Hauser, J. Phys. Chem. 55 408 (1951); pendent drop method.
[c]J. L. Cayias, R. S. Schecter and W. H. Wade, in Adsorption at Interfaces (ed. by K. L. Mittal), ACS Symp. Ser. 8 (1975); spinning drop method.
[d]C. D. Manning, M.S. thesis, University of Minnesota (1976); spinning drop method.
[e]C. D. Manning, loc. cit.; sessile drop method.
[f]C. D. Manning, loc. cit.; pendent drop method.
[g]0.2 percent wt. Witco Co. petroleum sulfonate TRS10-80 dispersed in 1 percent wt. NaCl in water; the resulting solution/dispersion is loaded into the sample holder and an octane drop injected; any equilibration takes place in the forty-hour period until the drop reaches a diameter that remains constant for six hours.

NOVEL CONCEPTS AND ADVANTAGES

The spinning drop method depends on approaching gyrostatic equilibrium closely enough for reliable tension measurements. Gyrostatic equilibrium cannot in principle be attained totally owing to the earth's gravitational field. Moreover, departures are aggravated by vibrations, lack of coaxiality, and temperature gradients. These limitations were not adequately recognized in the prior art. The main points of novelty and advantage in this invention are the following:

1. Combined use of air bearings and precision axial mountings of sample holders in order to reduce vibrations and eccentricities, eliminate temperature gradients within the sample, and assure suppression of interfering hydrodynamic flows that were undetected or unappreciated in the prior art.
   a. Vibrations. The air bearings hydrodynamically center the spinning assembly and, with careful dynamic balancing, practically remove radial vibrations. The timing belt transmission protects against vibrations generated in the motor shaft. Axial vibration is effectively eliminated by employing axial thrust of air escaping from the air bearings past positioning discs, aided if necessary by an axial air jet.
   b. Coaxiality. The spindle mounting ensures coincidence of the axis of the inner surface of the sample holder and the axis of rotation. The alternative receptacle mounting, though it enforces coaxiality slightly less well, conveniently allows sample holders to be interchanged in a single shaft.

2. Use of sample holders of biprecision glass tubing of high precision, i.e., accurately round with inside and outside surfaces virtually concentric in order to eliminate azimuthally varying optical distortion of the spinning drop, so that its diameter can be measured accurately without needing a stroboscope. This is only possible because (1) has been achieved.

3. Measurement of refractive index of the denser fluid rather than determination of magnification factors for drops, a tedious and much less accurate procedure. This is only possible in precise measurements of interfacial tension because (2) has been achieved.

4. Mounting of sample holders to allow them to be viewed from any direction at all times, so that flows are readily detected within the sample holder, and thereby any departures from the gyrostatic equilibrium necessary for precise measurement of interfacial tension. This feature also makes it easy to control the sample temperature by bathing the sample holder in the thermostated air.

5. Locating the entire apparatus within a thermostated bath of dry air and supplying the bearings with air at the same temperature, so that measurements can conveniently be made at temperatures substantially different from ambient.

6. Provision of standard three-point leveling means for bringing the axis of rotation of the sample holder closer to horizontal than had been recognized as desirable in the prior art, owing to interference by other, greater sources of error.

7. Use of timing belt to avoid any possibility of slippage in the speed-up linkage between motor and main shaft of the instrument, and thereby to ensure more accurate speed control than had been recognized as desirable in the prior art.

8. Multiway switching that allows one frequency counter to be used to measure speeds of four or more instruments in cyclic sequence; similar provision for using one stroboscope, when desired, in cyclic sequence with four or more instruments; and a design that allows one measuring microscope to be shared among four or more instruments. These features are particularly cost effective.

It is apparent that many modifications and variations of this invention as hereinbefore set forth may be made without departing from the spirit and scope thereof. The specific embodiments described are given by way of example only and the invention is limited only by the terms of the appended claims.

The embodiments of the invention in which an exclusive property or privilege is claimed are defined as follows:

1. An instrument for measuring interfacial tension between two fluids of different density by means of a drop of the less dense fluid surrounded by the more dense fluid, both fluids spinning together in gyrostatic equilibrium, said instrument comprising:
   (A) a massive bearing housing adapted to be supported on a massive base having three-point leveling means,
      (1) a pair of porous bushings tandemly aligned within said bearing housing, (2) compressed air inlet and outlet ports in said bearing housing,
(3) a precision ground shaft journaled in said bushings,
(4) means for measuring the rotation of said shaft, and
(5) means for positioning said shaft axially in said housing,
(B) a biprecision transparent isothermal sample tube rigidly secured at one end to one end of said shaft for precisely co-axial rotation therewith,
(1) sealing means closing the opposite end of said sample tube,
(C) a sample holder housing enclosing said sample tube,
(1) said sample holder housing removably secured to said bearing housing,
(2) aligned windows in said sample holder housing permitting viewing of said sample tube,
(3) temperature control gas inlet and outlet ports in said sample holder housing, and
(D) power means for rotating said shaft and sample tube at a constant rotational speed sufficient to maintain gyrostatic equilibrium.

2. An instrument according to claim 1 wherein said means for measuring the rotation of said shaft comprises:
(A) a dynamically balanced slotted disc mounted for rotation with said shaft, and
(B) a fixed rotation sensor mounted astride the periphery of said disc.

3. An instrument according to claim 2 wherein:
(A) said disc has a radially extending peripheral slot and a diametrically opposed dynamically compensating hole, and
(B) said rotation sensor is a photon-coupled interruptor module.

4. An instrument according to claim 1 wherein:
(A) said shaft has an integral precisely ground precisely co-axial spindle extending from one end thereof,
(B) one end of the bore of said sample tube is fitted over said spindle and rigidly secured thereto, and
(C) sealing means are provided between said bore and the end of said spindle.

5. An instrument according to claim 4 wherein said spindle is grooved and said sample tube is cemented to the grooved spindle.

6. An instrument according to claim 4 wherein said means for positioning the shaft axially in the bearing housing comprises:
(A) a dynamically balanced disc mounted for rotation with said shaft and closely spaced from the end of the porous bushing at the driven end of the shaft, and
(B) an axial air jet directed against the driven end of the shaft.

7. An instrument according to claim 1 wherein:
(A) a precisely bored precisely co-axial tube receptacle is provided in one end of said shaft,
(B) said sample tube is closed at one end, and
(C) the closed end of said sample tube is received into and rigidly secured in said receptacle.

8. An instrument according to claim 7 wherein said means for positioning the shaft axially in the bearing housing comprises a pair of dynamically balanced discs, each mounted to rotate with said shaft and located closely spaced from the outside opposite ends of said porous bushings.

9. An instrument according to claim 1 wherein:
(A) said sample tube has an outside peripheral groove adjacent the open end thereof,
(B) said sealing means comprises:
(1) a cap enclosing the open end of the tube,
(2) an internally extending flanged lip on said cap engaging the groove in said tube,
(3) a resilient disc between the end of said tube and the inside of said cap, and
(4) a hole in said cap co-axial with the bore of the tube.

10. An instrument according to claim 1 wherein said sample holder housing is transparent.

11. An instrument according to claim 1 wherein each of the windows in said sample holder housing is fitted with an optically flat glass window pane.

12. An instrument according to claim 1 wherein said power means comprises:
(A) an electric motor fitted with a cogged drive pulley,
(B) a timing belt pulley secured to said shaft, and
(C) a timing belt interconnecting said pulleys.

* * * * *

UNITED STATES PATENT AND TRADEMARK OFFICE
CERTIFICATE OF CORRECTION

PATENT NO. : 4,250,741
DATED : February 17, 1981
INVENTOR(S) : L. Edward Scriven II et al It is certified that error appears in the above-identified patent and that said Letters Patent are hereby corrected as shown below:

On the title page, the following statement is omitted:

--The Government has rights in this invention pursuant to Grant Number AER75-03522 awarded by the National Science Foundation.--

Column 4, line 15, "seal-sealing" snould be --self-sealing--.

Signed and Sealed this

Ninth Day of June 1981

[SEAL]

Attest:

RENE D. TEGTMEYER

Attesting Officer

Acting Commissioner of Patents and Trademarks